US010717805B2

(12) United States Patent
Matner et al.

(10) Patent No.: US 10,717,805 B2
(45) Date of Patent: Jul. 21, 2020

(54) PROCESS FOR PRODUCING POLYISOCYANURATE PLASTICS

(71) Applicant: Covestro Deutschland AG, Leverkusen (DE)

(72) Inventors: Mathias Matner, Neuss (DE); Dirk Achten, Leverkusen (DE); Hans-Josef Laas, Odenthal (DE); Heiko Hocke, Shanghai (CN); Dieter Mager, Leverkusen (DE)

(73) Assignee: Covestro Deutschland AG, Leverkusen (DE)

( * ) Notice: Subject to any disclaimer, the term of this patent is extended or adjusted under 35 U.S.C. 154(b) by 0 days.

(21) Appl. No.: 15/568,101

(22) PCT Filed: Apr. 21, 2016

(86) PCT No.: PCT/EP2016/058902
§ 371 (c)(1),
(2) Date: Oct. 20, 2017

(87) PCT Pub. No.: WO2016/170058
PCT Pub. Date: Oct. 27, 2016

(65) Prior Publication Data
US 2018/0079855 A1 Mar. 22, 2018

(30) Foreign Application Priority Data
Apr. 21, 2015 (EP) .................................... 15164519

(51) Int. Cl.
C08G 18/79 (2006.01)
C08G 18/02 (2006.01)
C07D 251/34 (2006.01)
C08G 18/09 (2006.01)
C08G 18/32 (2006.01)

(52) U.S. Cl.
CPC ......... C08G 18/792 (2013.01); C07D 251/34 (2013.01); C08G 18/022 (2013.01); C08G 18/027 (2013.01); C08G 18/09 (2013.01); C08G 18/32 (2013.01)

(58) Field of Classification Search
CPC ... C08G 18/792; C08G 18/022; C08G 18/027
See application file for complete search history.

(56) References Cited

U.S. PATENT DOCUMENTS

| 3,211,703 | A | 10/1965 | Gilman et al. |
| 3,330,828 | A | 7/1967 | Grogler et al. |
| 3,487,080 | A | 12/1969 | Matsui et al. |
| 3,640,937 | A | 2/1972 | Thoma et al. |
| 3,640,967 | A | 2/1972 | König et al. |
| 3,658,746 | A | 4/1972 | Rosendahl et al. |
| 3,996,223 | A | 12/1976 | Gupta et al. |
| 4,040,992 | A | 8/1977 | Bechara et al. |
| 4,255,569 | A | 3/1981 | Müller et al. |
| 4,288,586 | A | 9/1981 | Bock et al. |
| 4,324,879 | A | 4/1982 | Bock et al. |
| 4,379,905 | A | 4/1983 | Stemmler et al. |
| 4,419,513 | A | 12/1983 | Breidenbach et al. |
| 4,487,928 | A | 12/1984 | Richter et al. |
| 4,499,253 | A | 2/1985 | Kerimis et al. |
| 4,604,418 | A | 8/1986 | Shindo et al. |
| 4,613,686 | A | 9/1986 | König et al. |
| 4,789,705 | A | 12/1988 | Kase et al. |
| 4,808,691 | A | 2/1989 | König et al. |
| 4,837,359 | A | 6/1989 | Woynar et al. |
| 4,960,848 | A | 10/1990 | Scholl et al. |
| 4,994,541 | A | 2/1991 | Dell et al. |
| 5,013,838 | A | 5/1991 | Scholl |
| 5,064,960 | A | 11/1991 | Pedain et al. |
| 5,076,958 | A | 12/1991 | Pedain et al. |
| 5,489,663 | A | 2/1996 | Brandt et al. |
| 5,914,383 | A | 6/1999 | Richter et al. |
| 6,090,939 | A | 7/2000 | Richter et al. |
| 6,133,397 | A | 10/2000 | O'Connor et al. |
| 6,251,985 | B1 | 6/2001 | Wamprecht et al. |
| 6,613,863 | B2 | 9/2003 | Kohlstruk et al. |
| 6,635,761 | B1 | 10/2003 | Revelant et al. |
| 6,765,111 | B1* | 7/2004 | Pedain ................. C07D 251/34 544/193 |
| 8,119,799 | B2 | 2/2012 | Binder et al. |
| 2009/0234091 | A1* | 9/2009 | Richter ............... B01J 31/0267 528/51 |
| 2010/0056702 | A1 | 3/2010 | Grahl et al. |
| 2011/0201709 | A1* | 8/2011 | Athey ................. C08G 18/022 521/128 |
| 2013/0303758 | A1 | 11/2013 | Lucas et al. |
| 2015/0158966 | A1 | 6/2015 | Laas et al. |
| 2017/0044296 | A1 | 2/2017 | Harada |

FOREIGN PATENT DOCUMENTS

| CA | 2034622 A1 | 8/1991 |
| CA | 2139535 A1 | 8/1995 |

(Continued)

OTHER PUBLICATIONS

Cinnamon, S., et al., "Adhesion Properties of Poly(Hexamethylene Diisocyanate) Obtained by Organotin Catalysis", European Polymer Journal, 1908, vol. 16, pp. 147-148.

(Continued)

Primary Examiner — Michael L Leonard
(74) Attorney, Agent, or Firm — Faegre Drinker Biddle & Reath LLP

(57) ABSTRACT

The invention relates to a process for producing polyisocyanurate plastics, comprising the following steps: (a) providing a polyisocyanate composition A) which contains oligomeric polyisocyanates and is low in monomeric diisocyanates, where the isocyanurate structure content in the polyisocyanate composition A) is at least 50 mol %, based on the sum total of the oligomeric structures from the group consisting of uretdione, isocyanurate, allophanate, biuret, iminooxadiazinedione and oxadiazinetrione structure that are present in the polyisocyanate composition A); (b) catalytically trimerizing the polyisocyanate composition A), where (i) the catalytic trimerization is conducted at ambient temperatures of at least 80° C.; (ii) the catalytic trimerization is conducted within less than 12 hours at least up to a degree of conversion at which only still not more than 20% of the isocyanate groups originally present in the polyisocyanate composition A) are present. Furthermore, the invention relates to a polyisocyanurate plastic obtainable by the process of the invention, to its use for producing coatings, films, semi-finished products and moldings.

20 Claims, No Drawings

(56) References Cited

FOREIGN PATENT DOCUMENTS

| | | |
|---|---|---|
| CA | 2244486 A1 | 2/1999 |
| CA | 2253119 A1 | 5/1999 |
| DE | 1570540 A1 | 3/1970 |
| DE | 1954093 A1 | 6/1970 |
| DE | 1902931 A1 | 8/1970 |
| DE | 1918204 A1 | 9/1970 |
| DE | 1670666 A1 | 7/1971 |
| DE | 1770245 A1 | 10/1971 |
| DE | 1770591 A1 | 11/1971 |
| DE | 1667309 A1 | 9/1972 |
| DE | 2414413 A1 | 10/1975 |
| DE | 2446440 A1 | 4/1976 |
| DE | 2452532 A1 | 5/1976 |
| DE | 2631733 A1 | 2/1977 |
| DE | 2641380 A1 | 3/1978 |
| DE | 3100263 A1 | 8/1982 |
| DE | 3219608 A1 | 9/1983 |
| DE | 3240613 A1 | 5/1984 |
| DE | 8711301 U1 | 10/1987 |
| DE | 3700209 A1 | 7/1988 |
| DE | 3717060 A1 | 12/1988 |
| DE | 3900053 A1 | 7/1990 |
| DE | 3928503 A1 | 3/1991 |
| DE | 10142816 A1 | 7/2002 |
| EP | 0003765 A1 | 9/1979 |
| EP | 0010589 A1 | 5/1980 |
| EP | 0013880 A1 | 8/1980 |
| EP | 0033581 A1 | 8/1981 |
| EP | 0047452 A1 | 3/1982 |
| EP | 0056158 A1 | 7/1982 |
| EP | 0056159 A1 | 7/1982 |
| EP | 0100129 A1 | 2/1984 |
| EP | 0102482 A2 | 3/1984 |
| EP | 0150769 A2 | 8/1985 |
| EP | 0330966 A2 | 9/1989 |
| EP | 0336205 A2 | 10/1989 |
| EP | 0339396 A1 | 11/1989 |
| EP | 0377177 A1 | 7/1990 |
| EP | 0379914 A2 | 8/1990 |
| EP | 0443167 A1 | 8/1991 |
| EP | 0496208 A2 | 7/1992 |
| EP | 0668271 A1 | 8/1995 |
| EP | 0671426 A1 | 9/1995 |
| EP | 0798299 A1 | 10/1997 |
| EP | 0896009 A1 | 2/1999 |
| EP | 0899282 A2 | 3/1999 |
| EP | 0916647 A2 | 5/1999 |
| EP | 0962455 A1 | 12/1999 |
| EP | 1229016 A2 | 8/2002 |
| EP | 1599526 A1 | 11/2005 |
| EP | 2159238 A1 | 3/2010 |
| EP | 2883895 A1 | 6/2015 |
| GB | 809809 A | 3/1959 |
| GB | 952931 A | 3/1964 |
| GB | 966338 A | 8/1964 |
| GB | 1145952 A | 3/1969 |
| GB | 1244416 A | 9/1971 |
| GB | 1335958 A | 10/1973 |
| GB | 1386399 A | 3/1975 |
| GB | 1391066 A | 4/1975 |
| GB | 1462597 A | 1/1977 |
| GB | 2221465 A | 2/1990 |
| GB | 2222161 A | 2/1990 |
| JP | S59059716 A | 4/1984 |
| JP | S59100179 A | 6/1984 |
| JP | 2001098042 A | 4/2001 |
| WO | WO-1999023128 A1 | 5/1999 |
| WO | WO-2004078820 A1 | 9/2004 |
| WO | WO-2005087828 A1 | 9/2005 |
| WO | WO-2013167404 A1 | 11/2013 |
| WO | WO-2015166983 A1 | 11/2015 |

OTHER PUBLICATIONS

Dabi, S., et al., "Foam Polymerization of Hexamethylene Diisocyanate by Cobalt Naphthenate", European Polymer Journal, 1982, vol. 18, pp. 549-553.

Dabi, S., et al., "Oligotrimerization of Hexamethylene Diisocyanate by Organometiallic Catalysts", European Polymer Journal, 1980, vol. 16, pp. 831-833.

Flipsen, T., "Design, Synthesis and Properties of New Materials Based on Densely Crosslinked Polymers for Polymer Optical Fiber and Amplifier Applications", Rijksuniversiteit Groningen, University of Groningen, 2000, pp. 1-231.

Hakman, N., "Properties of Polyisocyanurate Resins Obtained by Polymerization of Hexamethylene Diisocyanate by Organotin Catalysts", European Polymer Journal, 1978, vol. 14, pp. 675-678.

Moritsugu, M., et al., "Cyclotrimerization of Diisocyanates Toward High-Performance Networked Polymers with Rigid Isocyanurate Structure: Combination of Aromatic and Aliphatic Diisocyanates for Tunable Flexibility", Journal of Polymer Science, 2013, vol. 51, pp. 2631-2637.

Schildknecht, C.E., et al., "Polymerization Processes", Wiley, New York, 1977, pp. 665-667.

International Preliminary Report on Patentability for PCT/EP2016/058901 dated Oct. 24, 2017.

International Preliminary Report on Patentability for PCT/EP2016/058902 dated Oct. 24, 2017.

International Preliminary Report on Patentability for PCT/EP2016/058904 dated Oct. 24, 2017.

International Preliminary Report on Patentability for PCT/EP2016/058905 dated Oct. 24, 2017.

International Preliminary Report on Patentability for PCT/EP2016/058906 dated Oct. 24, 2017.

International Search Report for PCT/EP2016/058901 dated Jun. 30, 2016.

International Search Report for PCT/EP2016/058902 dated Jul. 14, 2016.

International Search Report for PCT/EP2016/058904 dated Jul. 13, 2016.

International Search Report for PCT/EP2016/058905 dated Jul. 8, 2016.

International Search Report for PCT/EP2016/058906 dated Jul. 13, 2016.

Written Opinion of the International Searching Authority for PCT/EP2016/058901 dated Jun. 30, 2016.

Written Opinion of the International Searching Authority for PCT/EP2016/058902 dated Jul. 14, 2016.

Written Opinion of the International Searching Authority for PCT/EP2016/058904 dated Jul. 13, 2016.

Written Opinion of the International Searching Authority for PCT/EP2016/058905 dated Jul. 8, 2016.

Written Opinion of the International Searching Authority for PCT/EP2016/058906 dated Jul. 13, 2016.

\* cited by examiner

PROCESS FOR PRODUCING POLYISOCYANURATE PLASTICS

CROSS-REFERENCE TO RELATED APPLICATIONS

This application is a national stage application (under 35 U.S.C. § 371) of PCT/EP2016/058902, filed Apr. 21, 2016, which claims benefit of European Application No. 15164519.9, filed, both of which are incorporated herein by reference in their entirety.

BACKGROUND OF THE INVENTION

The invention relates to polyisocyanurate plastics, to a process for producing the polyisocyanurate plastics of the invention, and to the use thereof for producing coatings, films, semi-finished products or mouldings.

Polymers having polyisocyanurate structure are known for their high thermal and flame stability. Polyisocyanurate-containing foams based on aromatic diphenylmethane 4,4'-diisocyanate (MDI) and polyetherpolyols and polyepoxides are widespread particularly as high-performance insulating materials for example on account of their low heat conductivity. See C. E. Schildknecht and I. Skeist, *Polymerization Processes*, pp. 665-667, Wiley, New York (1977). However, MDI-polyisocyanurate-containing foams, as is generally known of aromatic polyurethanes, have only low light stability and a tendency towards severe yellowing.

There has therefore been no lack of attempts to synthesize polyisocyanurate plastics based on aliphatic light-resistant isocyanates.

For example, *European Polymer Journal*, vol. 16, 147-148 (1980) describes the catalytic trimerization of monomeric 1,6-diisocyanatohexane (HDI) at 40° C. to give a clear transparent polyisocyanurate plastic free of isocyanate groups. For this, however, 15% by weight of dibutyltin dimethoxide are required as trimerization catalyst, and this has a severe negative impact on the thermal stability and colour stability of the products. *European Polymer Journal*, Vol. 16, 831-833 (1980) describes the complete trimerization of monomeric HDI to give a polyisocyanurate at a temperature of 140° C. using 6% by weight of tributyltin oxide as catalyst.

The thesis by Theo Flipsen: "*Design, synthesis and properties of new materials based on densely crosslinked polymers for polymer optical fiber and amplifier applications*", Rijksuniversiteit Groningen, 2000 describes the trimerization of monomeric HDI with a neodymium/crown ether complex as catalyst. The polyisocyanurate obtained, which is said to have good optical, thermal and mechanical properties, was studied in the context of the thesis for its suitability for optical applications, especially as polymeric optical fibres. Flipsen gives a detailed description of the prerequisites for clear non-yellowed polyisocyanurates. Explicit mention should be made here of avoidance of impurities, water, dimers, high catalyst concentration and high temperatures at the start of the reaction. Troublesome side reactions are the reaction with water to give ureas, and of uretdiones to give carbodiimides with blister formation. According to Flipsen, high transparency polyisocyanurates with a $T_g$ of 140° C. are obtained only under ideal conditions with a soluble neodymium/crown ether catalyst and a pre-reaction at room temperature or 60° C. or room temperature and post reaction at temperatures of up to 140° C. over a long period of more than 24 h. A disadvantage of the described process is that it is a time-consuming multistage process with complicated reaction regime, the large-scale conversion of which is problematic.

The subject of Moritsugu, M., Sudo, A. and Endo, T., J. Polym. Sci. A Polym. Chem. 2013, 51, 2631-2637, is the polymerization of monomeric HDI and MDI with Na-paratolyl sulphonate in various ratios in DMI solution at 150° C. Primarily, clear and colourless products are obtained which, following the reaction, have to be powdered and be purified by means of Soxhlet extraction of solvents and unreacted constituents. In the case of pure HDI, a conversion of 94% is obtained following extraction of 6% soluble fractions. The polyisocyanurate has a $T_g$ of 115° C. The trimerization is conducted in amounts of approx. 1 g in the 25 ml flask. The process thus described is technically problematic on account of the multistage process and the high fraction of extractable components.

The production of polyisocyanurates is described in the prior art primarily starting from liquid monomeric diisocyanates (e.g. stearyl diisocyanate, dodecyl diisocyanate, decyl diisocyanate, nonyl diisocyanate, octyl diisocyanate, HDI, BDI, PDI, IPDI, H12MDI, TDI, MDI, NDI, NBDI), of aliphatic and aromatic nature. The heat tonality of the trimerization reaction to polyisocyanurates is so high (−75 kJ/mol NCO) that a reaction starting from monomeric diisocyanates, particularly in the case of monomeric diisocyanates with high isocyanate content (e.g. BDI, PDI, HDI, TIN), can typically not be conducted on an industrial scale and under adiabatic conditions as typically arise in the inside of volume bodies during strongly exothermic polymerization processes, but only in small quantitative amounts under strict temperature control.

"Adiabatic conditions" means here in particular that a complete dissipation of the heat of reaction released during the exothermic reaction to the surrounding area is not possible. Thus, typically no homogeneous conditions can be realised in volume bodies and adiabatic conditions prevail particularly in the inside of the volume bodies which can lead, in the case of an exothermic reaction, to a considerable local temperature increase. These local hotspots are extremely critical if it is a question of producing functionally homogeneous products.

A further problem is that aromatic monomeric diisocyanates and many arylaromatic or alicyclic monomeric diisocyanates can be homo- and co-trimerized only to low conversions. Often plasticizing or co-dissolving reactants have to be added. Otherwise, the reaction freezes at high residual isocyanate contents and typically opaque and discoloured products are obtained. The use of plasticizing and co-dissolving reactants is again disadvantageous since these lead to less chemically and thermally inert structural elements such as allophanates, ureas, urethanes, thiourethanes and oxazolidinones, polyesters, polyethers, and at high temperatures to uretdiones with subsequent carbodiimidation and carbon dioxide elimination, and to asymmetric isocyanates. The production of polyisocyanurates having largely exclusively isocyanurate structures as structural element is therefore not possible.

Temperature control during the production of highly reacted polyisocyanurates is of enormous importance since, on account of the high isocyanate contents of the monomeric starting materials under adiabatic conditions, as typically prevail during trimerizations in volume bodies, on account of the exothermic reaction, temperatures of more than 300° C. can arise which may lead to the direct decomposition of the products and even to the in situ evaporation of the monomeric diisocyanates. Besides the occupational hygiene disadvantages due to the released toxic monomeric diisocyanates or decomposition products, the formation of blisters is very troublesome here.

Consequently, polyisocyanurates have hitherto usually only found practical applications as crosslinking agents in paint chemistry, the production of which involves stopping the trimerization reaction at low conversions and removing excess unreacted monomeric diisocyanate. Thus, DE 31 00 263; GB 952 931, GB 966 338; U.S. Pat. Nos. 3,211,703, 3,330,828 envisage conducting the reaction either in dilution or only up to low conversion values with very precise temperature control during the production of crosslinking agents based on isocyanurates starting from aliphatic and mixed aliphatic and aromatic monomeric diisocyanates. There is deliberately no formation here of crosslinked polyisocyanurate plastics, but only of oligomeric, soluble products of low viscosity.

A common feature of the aforementioned processes is that the trimerization is started at low temperatures. Higher trimerization temperatures, particularly at the start of the trimerization, can be controlled only with difficulty starting from monomeric diisocyanates and lead to considerable side reactions in the form of uretdiones, carbodiimides, and also to blistering and discoloration.

Another common feature of the described processes is that they are unsuitable for obtaining highly converted polyisocyanurates with a low residual content of free isocyanate groups in efficient industrial processes, especially those which are largely free from extractable monomers. Nor is it possible in this way, by the processes known from the prior art, to effect trimerization at elevated temperatures in open reaction vessels without risking significant release of monomeric diisocyanates into the environment.

WO 2015/166983 discloses the use of isocyanurate polymers for encapsulating LEDs. The use of carboxylates and alkoxides of alkali metals, alkaline earth metals or zirconium, in combination with complexing agents such as crown ethers or polyethylene glycols or polypropylene glycols, and organic tin compounds is not disclosed. Moreover, there is no particular disclosure for coating of specific substrates.

U.S. Pat. No. 6,133,397 discloses coatings made by trimerizing oligomeric polyisocyanates. However, the curing temperatures disclosed are significantly above room temperature.

BRIEF SUMMARY OF THE INVENTION

The object of the invention was therefore to develop an efficient industrial process for producing highly converted polyisocyanurates, especially those which are largely free from extractable and highly volatile monomeric constituents.

Surprisingly, it has been found that high-functionality liquid oligomeric polyisocyanates that are known as crosslinker raw materials in paint chemistry can be trimerized quickly and efficiently, even under adiabatic conditions, to give highly converted polyisocyanurates with excellent thermal, optical and mechanical properties.

Compared to the processes known from the prior art for producing polyisocyanurates based on monomeric diisocyanates, with the process of the invention it is possible to considerably reduce the impact on the environment with volatile isocyanates, even in the case of reaction in open vessels and on surfaces even at high reaction temperatures. The reason for this is especially because no monomeric diisocyanates are used. Even at the gel point, the process of the invention gives rise to homogeneous products with a considerably lower concentration of extractable isocyanate-containing constituents. The gel point is understood to mean the juncture at which the crosslinking density in the reaction mixture is so far advanced that the viscosity of the reaction mixture rises abruptly and the reaction mixture gelates, i.e. no longer significantly deforms or flows. The processes described in the prior art reach the gel point only at much higher isocyanate conversions of well above 50%, since a crosslinking density sufficient for gelation, proceeding from monomeric diisocyanates having isocyanate functionalities of less than or equal to two, i.e. less than or equal to two isocyanate groups per molecule, is statistically achieved only at higher isocyanate conversions. By contrast, the use of oligomeric polyisocyanates with isocyanate functionalities greater than two, i.e. more than two isocyanate groups per molecule, statistically results in a high crosslinking density at a much earlier stage, meaning that gellation of the reaction mixture is achieved at lower conversions and hence much earlier. Moreover, the processes described in the prior art, even well after the gel point, still have extractable isocyanate-containing constituents.

As a departure from the processes described in the prior art, the trimerization in accordance with the process of the invention can also be carried out at high temperatures of more than 80° C. With comparatively short reaction times below 12 h, it is possible by the process of the invention to obtain blister-free and transparent products with low discoloration.

Particularly advantageously, the trimerization can be conducted at temperatures above the glass transition point of the desired products.

By means of the process of the invention it is possible to obtain polyisocyanurate plastics which differ physically, for example in the glass transition temperature, from the products based on monomeric diisocyanates described in the prior art. Without wishing to be bound to scientific theories, this is probably based on structural differences in the nature and density of the crosslinking in the polyisocyanurate plastic obtained, which is attributable to the use of oligomeric polyisocyanates and to the particular reaction regime.

The invention thus provides a process for producing polyisocyanurate plastics, wherein it comprises the following steps:
a) providing a polyisocyanate composition A) which contains oligomeric polyisocyanates and is low in monomeric polyisocyanates, where the isocyanurate structure content in the polyisocyanate composition A) is at least 50 mol %, based on the sum total of the oligomeric structures from the group consisting of uretdione, isocyanurate, allophanate, biuret, iminooxadiazinedione and oxadiazinetrione structure that are present in the polyisocyanate composition A);
b) catalytically trimerizing the polyisocyanate composition A), where
   (i) the catalytic trimerization is conducted at ambient temperatures of at least 80° C.;
   (ii) the catalytic trimerization is conducted within less than 12 hours at least up to a degree of conversion at which only still not more than 20% of the isocyanate groups originally present in the polyisocyanate composition A) are present.

The invention further provides the polyisocyanurate plastics obtainable by the process, and the use thereof for producing coatings, films, semi-finished products, mouldings. Moreover, the invention also provides coatings, films, semi-finished products and mouldings containing a polyisocyanurate plastic obtainable by the process.

DETAILED DESCRIPTION OF THE INVENTION

The invention, described in more detail below, is based on the surprising observation that by means of catalytic trimerization of low-monomer oligomeric polyisocyanate compositions A) with at least 50 mol % isocyanurate structure content based on the sum total of the present oligomeric structures from the group consisting of uretdione, isocyanurate, allophanate, biuret, iminooxadiazinedione and oxadiazinetrione structure in the polyisocyanate composition A), at ambient temperatures of more than 80° C. and with short reaction times of less than 12 h, it is possible to obtain new types of polyisocyanurate plastics which have many advantageous properties and in particular exhibit an only comparatively small volume shrinkage during the curing process.

The use of low-monomer oligomeric polyisocyanate compositions instead of monomeric diisocyanates as starting materials for producing polyisocyanurate plastics, moreover, has the advantage that, on account of the lower isocyanate contents of the oligomeric starting materials, a considerably lesser heat of reaction has to be dissipated during the curing, which in particular permits a rapid trimerization reaction with short reaction times of less than 12 h and at high temperatures above 80° C. Moreover, the use of low-monomer polyisocyanate compositions containing oligomeric polyisocyanates as oligomeric reactants for the trimerization reaction also leads to a novel crosslinking structure in the polyisocyanurate plastic obtainable, which distinguishes it structurally from the materials known from the prior art.

A "polyisocyanurate plastic" as used here is a polymer containing polyisocyanurate. It may also consist predominantly or entirely of a polyisocyanurate. Blends of polyisocyanurates and other plastics are likewise covered by the term "polyisocyanurate plastic" as used here.

When reference is made here to "plastic", this means a product which is very substantially dimensionally stable at room temperature—in contrast, for example, to gels or liquids. The term "plastic", as used here, includes all customary classes of plastic, i.e. in particular including thermosets, thermoplastics and elastomers.

A "polyisocyanurate" as used here is any molecule, preferably a polymer, having a plurality of isocyanurate structural units, for example at least ten isocyanurate structural units. A molecule having a single isocyanurate structural unit can be referred to as "isocyanurate".

The characteristic cyclic isocyanurate structural unit is shown in the following structural formula:

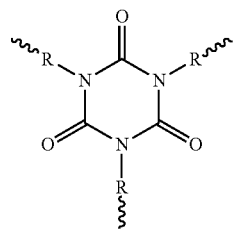

Isocyanurates and polyisocyanurates can be obtained by cyclotrimerization of polyisocyanates. The conventionally operated cyclotrimerization proceeding from monomeric diisocyanates is—as described above—a strongly exothermic reaction. This can considerably restrict the use options and the levels of trimerization that are still achievable industrially and efficiently.

The term "polyisocyanate" as used here is a collective term for compounds containing two or more isocyanate groups in the molecule (this is understood by the person skilled in the art to mean free isocyanate groups of the general structure —N═C═O). The simplest and most important representatives of these polyisocyanates are the diisocyanates. These have the general structure O═C═N—R—N═C═O where R typically represents aliphatic, alicyclic and/or aromatic radicals.

Because of the polyfunctionality (≥2 isocyanate groups), it is possible to use polyisocyanates to prepare a multitude of polymers (e.g. polyurethanes, polyureas and polyisocyanurates) and low molecular weight compounds (for example those having uretdione, isocyanurate, allophanate, biuret, iminooxadiazinedione and/or oxadiazinetrione structure).

When general reference is made here to "polyisocyanates", this means monomeric and/or oligomeric polyisocyanates alike. For understanding of many aspects of the invention, however, it is important to distinguish between monomeric diisocyanates and oligomeric polyisocyanates. When reference is made here to "oligomeric polyisocyanates", this means polyisocyanates formed from at least two diisocyanate molecules, i.e. compounds that constitute or contain a reaction product formed from at least two diisocyanate molecules.

The preparation of oligomeric polyisocyanates from monomeric diisocyanates is also referred to here as modification of monomeric diisocyanates. This "modification" as used here means the reaction of monomeric diisocyanates to give oligomeric polyisocyanates having uretdione, isocyanurate, allophanate, biuret, iminooxadiazinedione and/or oxadiazinetrione structure.

For example, hexamethylene diisocyanate (HDI) is a "monomeric diisocyanate" since it contains two isocyanate groups and is not a reaction product of at least two polyisocyanate molecules:

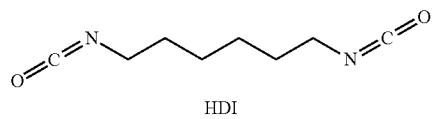

HDI

Reaction products which are formed from at least two HDI molecules and still have at least two isocyanate groups, by contrast, are "oligomeric polyisocyanates" within the context of the invention. Representatives of such "oligomeric polyisocyanates" are, proceeding from monomeric HDI, for example, HDI isocyanurate and HDI biuret, each of which is formed from three monomeric HDI units:

(idealized structural formulae)

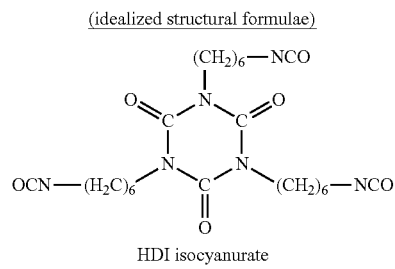

HDI isocyanurate

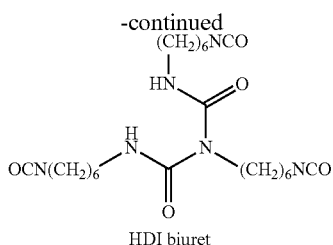

HDI biuret

"Polyisocyanate composition A)" in the context of the invention refers to the isocyanate component in the initial reaction mixture. In other words, this is the sum total of all the compounds in the initial reaction mixture that have isocyanate groups. The polyisocyanate composition A) is thus used as reactant in the process of the invention. When reference is made here to "polyisocyanate composition A)", especially to "providing the polyisocyanate composition A)", this means that the polyisocyanate composition A) exists and is used as reactant.

According to the invention, the polyisocyanate composition A) used in the trimerization is low in monomers (i.e. low in monomeric diisocyanates) and contains oligomeric polyisocyanates. In one embodiment of the invention, the polyisocyanate composition A) consists entirely or to an extent of 80%, 85%, 90%, 95%, 98%, 99% or 99.5% by weight, based in each case on the weight of the polyisocyanate composition A), of oligomeric polyisocyanates. This content of oligomeric polyisocyanates is based on the polyisocyanate composition A), meaning that they are not formed, for instance, as intermediate during the process of the invention, but are already present in the polyisocyanate composition A) used as reactant on commencement of the reaction.

"Low in monomers" and "low in monomeric diisocyanates" are used synonymously here in relation to the polyisocyanate composition A).

Results of particular practical relevance are established when the polyisocyanate composition A) has a proportion of monomeric diisocyanates in the polyisocyanate composition A) of not more than 20% by weight, especially not more than 15% by weight or not more than 10% by weight, based in each case on the weight of the polyisocyanate composition A). Preferably, the polyisocyanate composition A) has a content of monomeric diisocyanates of not more than 5% by weight, especially not more than 2.0% by weight, more preferably not more than 1.0% by weight, based in each case on the weight of the polyisocyanate composition A). Particularly good results are established when the polymer composition A) is essentially free of monomeric polyisocyanates. "Essentially free" means that the content of monomeric polyisocyanates is not more than 0.5% by weight, based on the weight of the polyisocyanate composition A).

It is essential to the invention that the polyisocyanate composition A) used is a low-monomer composition. In practice, this can especially be achieved by using, as polyisocyanate composition A), oligomeric polyisocyanates whose preparation involves, after the actual modification reaction, at least one further process step in each case for removal of the unconverted excess monomeric diisocyanates. In a manner of particular practical relevance, this monomer removal can be effected by processes known per se, preferably by thin-film distillation under high vacuum or by extraction with suitable solvents that are inert toward isocyanate groups, for example aliphatic or cycloaliphatic hydrocarbons such as pentane, hexane, heptane, cyclopentane or cyclohexane.

In a preferred embodiment of the invention, the polyisocyanate composition A) of the invention is obtained by modification of monomeric diisocyanates with subsequent removal of unconverted monomers.

The processes for producing polyisocyanurate plastics described in the prior art use very substantially monomeric diisocyanates as reactants, meaning that pure monomers or monomer-rich polyisocyanate compositions are catalytically trimerized. In contrast to this, the use according to the invention of a low-monomer polyisocyanate composition A) which already contains oligomeric polyisocyanates surprisingly leads to a significantly lower volume shrinkage. The relatively low exothermicity of the inventive reaction additionally allows polyisocyanurate plastics with a high conversion level to be obtained.

Preferably, no monomeric diisocyanate is used in the trimerization reaction of the invention. In a particular embodiment of the invention, however, the polyisocyanate composition A) may contain an extra monomeric diisocyanate. In this context, "extra monomeric diisocyanate" means that it differs from the monomeric diisocyanates which have been used for preparation of the oligomeric polyisocyanates present in the polyisocyanate composition A). Addition of extra monomeric diisocyanate may be advantageous for achievement of special technical effects, for example an exceptional hardness. Results of particular practical relevance are established when the polyisocyanate composition A) has a proportion of extra monomeric diisocyanate in the polyisocyanate composition A) of not more than 20% by weight, especially not more than 15% by weight or not more than 10% by weight, based in each case on the weight of the polyisocyanate composition A). Preferably, the polyisocyanate composition A) has a content of extra monomeric diisocyanate of not more than 5% by weight, preferably not more than 2.0% by weight, particularly preferably not more than 1.0% by weight, in each case based on the weight of the polyisocyanate composition A).

In a further particular embodiment of the process of the invention, the polyisocyanate composition A) may contain monomeric monoisocyanates or monomeric isocyanates having an isocyanate functionality greater than two, i.e. having more than two isocyanate groups per molecule. The addition of monomeric monoisocyanates or monomeric isocyanates having an isocyanate functionality greater than two has been found to be advantageous in order to influence the network density of the polyisocyanurate plastic. Results of particular practical relevance are established when the polyisocyanate composition A) has a proportion of monomeric monoisocyanates or monomeric isocyanates having an isocyanate functionality greater than two in the polyisocyanate composition A) of not more than 20% by weight, especially not more than 15% by weight or not more than 10% by weight, based in each case on the weight of the polyisocyanate composition A). Preferably, the polyisocyanate composition A) has a content of monomeric monoisocyanates or monomeric isocyanates having an isocyanate functionality greater than two of not more than 5% by weight, especially not more than 2.0% by weight, more preferably not more than 1.0% by weight, based in each case on the weight of the polyisocyanate composition A). Preferably, no monomeric monoisocyanate or monomeric isocyanate having an isocyanate functionality greater than two is used in the trimerization reaction of the invention.

The low-monomer polyisocyanate composition A) and the oligomeric polyisocyanates present therein are typically obtained by modifying simple aliphatic, cycloaliphatic, araliphatic and/or aromatic monomeric diisocyanates or mixtures of such monomeric diisocyanates.

The oligomeric polyisocyanates may, in accordance with the invention, especially have uretdione, isocyanurate, allophanate, biuret, iminooxadiazinedione and/or oxadiazinetrione structure. In one embodiment of the invention, the oligomeric polyisocyanates have at least one of the following oligomeric structure types or mixtures thereof:

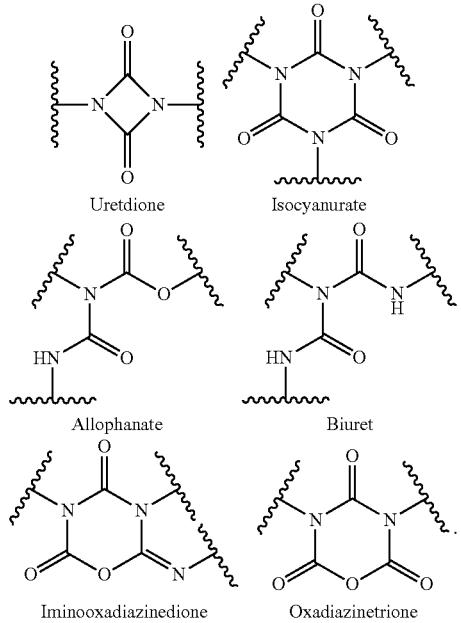

Uretdione
Isocyanurate
Allophanate
Biuret
Iminooxadiazinedione
Oxadiazinetrione

Surprisingly, it has been found that it may be advantageous for the reaction regime of the trimerization to use a polyisocyanate composition A) whose isocyanurate structure content is at least 50 mol %, based on the sum total of the oligomeric structures from the group consisting of uretdione, isocyanurate, allophanate, biuret, iminooxadiazinedione and oxadiazinetrione structure that are present in the polyisocyanate composition A). Especially compared to trimerization reactions with polyisocyanate compositions A), the isocyanurate structure content of which is less than 50 mol %, based on the sum total of the oligomeric structures from the group consisting of uretdione, isocyanurate, allophanate, biuret, iminooxadiazinedione and oxadiazinetrione structure that are present in the polyisocyanate composition A), starting mixtures of this type can be converted at high temperatures above 80° C. and with short reaction times of less than 12 h to give highly converted polyisocyanurate plastics.

In a preferred embodiment of the invention, a polymer composition A) is used, the isocyanurate structure content of which is at least 60 mol %, preferably 70 mol %, more preferably 80 mol %, particularly preferably 90 mol %, in particular 95 mol %, based on the sum total of the oligomeric structures from the group consisting of uretdione, isocyanurate, allophanate, biuret, iminooxadiazinedione and oxadiazinetrione structure that are present in the polyisocyanate composition A).

In an additional or alternative embodiment, a polyisocyanate composition A) which, besides the isocyanurate structure, contains at least one further oligomeric polyisocyanate with uretdione, biuret, allophanate, iminooxadiazinedione and oxadiazinetrione structure and mixtures thereof, is used in the process of the invention.

The proportions of uretdione, isocyanurate, allophanate, biuret, iminooxadiazinedione and/or oxadiazinetrione structure in the polyisocyanates A) can be determined, for example, by NMR spectroscopy. It is possible here with preference to use $^{13}C$ NMR spectroscopy, preferably in proton-decoupled form, since the oligomeric structures mentioned give characteristic signals.

Irrespective of the underlying oligomeric structure (uretdione, isocyanurate, allophanate, biuret, iminooxadiazinedione and/or oxadiazinetrione structure), the oligomeric polyisocyanate composition A) for use in the process of the invention and/or the oligomeric polyisocyanates present therein preferably have/has a (mean) NCO functionality of 2.0 to 5.0, preferably of 2.3 to 4.5.

Results of particular practical relevance are established when the polyisocyanate composition A) for use in accordance with the invention has a content of isocyanate groups of 8.0% by weight to 28.0% by weight, preferably of 14.0% to 25.0% by weight, based in each case on the weight of the polyisocyanate composition A).

Production processes for the oligomeric polyisocyanates with uretdione, isocyanurate, allophanate, biuret, iminooxadiazinedione and/or oxadiazinetrione structure to be used according to the invention in the polyisocyanate composition A) are described, for example, in J. Prakt. Chem. 336 (1994) 185-200, in DE-A 1 670 666, DE-A 1 954 093, DE-A 2 414 413, DE-A 2 452 532, DE-A 2 641 380, DE-A 3 700 209, DE-A 3 900 053 and DE-A 3 928 503 or in EP-A 0 336 205, EP-A 0 339 396 and EP-A 0 798 299.

In an additional or alternative embodiment of the invention, the polyisocyanate composition A) of the invention is defined in that it contains oligomeric polyisocyanates which have been obtained from monomeric diisocyanates, irrespective of the nature of the modification reaction used, with observation of an oligomerization level of 5% to 45%, preferably 10% to 40%, more preferably 15% to 30%. "Oligomerization level" is understood here to mean the percentage of isocyanate groups originally present in the starting mixture which are consumed during the preparation process to form uretdione, isocyanurate, allophanate, biuret, iminooxadiazinedione and/or oxadiazinetrione structures.

Suitable polyisocyanates for preparation of the polyisocyanate composition A) for use in the process of the invention and the oligomeric polyisocyanates present therein are any desired polyisocyanates obtainable in various ways, for example by phosgenation in the liquid or gas phase or by a phosgene-free route, for example by thermal urethane cleavage. Particularly good results are established when the polyisocyanates are monomeric diisocyanates. Preferred monomeric diisocyanates are those which have a molecular weight in the range from 140 to 400 g/mol, with aliphatically, cycloaliphatically, araliphatically and/or aromatically bonded isocyanate groups, such as e.g. 1,4-diisocyanatobutane (BDI), 1,5-diisocyanatopentane (PDI), 1,6-diisocyanatohexane (HDI), 2-methyl-1,5-diisocyanatopentane, 1,5-diisocyanato-2,2-dimethylpentane, 2,2,4 or 2,4,4-trimethyl-1,6-diisocyanatohexane, 1,10-diisocyanatodecane, 1,3 and 1,4-diisocyanatocyclohexane, 1,4-diisocyanato-3,3,5-trimethylcyclohexane, 1,3-diisocyanato-2-methylcyclohexane, 1,3-diisocyanato-4-methylcyclohexane, 1-isocyanato-3,3,5-trimethyl-5-isocyanatomethylcyclohexane (isophorone diisocyanate; IPDI), 1-isocyanato-1-methyl-4(3)-isocyanatomethylcyclohexane, 2,4' and 4,4'-diisocyanatodicyclohexylmethane (H12MDI), 1,3 and 1,4-bis(isocyanatomethyl)cyclohexane, bis(isocyanatomethyl)

norbornane (NBDI), 4,4'-diisocyanato-3,3'-dimethyldicyclohexylmethane, 4,4'-diisocyanato-3,3',5,5'-tetramethyldicyclohexylmethane, 4,4'-diisocyanato-1,1'-bi(cyclohexyl), 4,4'-diisocyanato-3,3'-dimethyl-1,1'-bi(cyclohexyl), 4,4'-diisocyanato-2,2',5,5'-tetramethyl-1,1'-bi(cyclohexyl), 1,8-diisocyanato-p-menthane, 1,3-diisocyanatoadamantane, 1,3-dimethyl-5,7-diisocyanatoadamantane, 1,3 and 1,4-bis(isocyanatomethyl)benzene (xyxlylene diisocyanate; XDI), 1,3 and 1,4-bis(1-isocyanato-1-methylethyl)benzene (TMXDI) and bis(4-(1-isocyanato-1-methylethyl)phenyl) carbonate, 2,4 and 2,6-diisocyanatotoluene (TDI), 2,4' and 4,4'-diisocyanatodiphenylmethane (MDI), 1,5-diisocyanatonaphthalene, and any desired mixtures of such diisocyanates. Further diisocyanates that are likewise suitable can additionally be found, for example, in *Justus Liebigs Annalen der Chemie*, volume 562 (1949) p. 75-136.

Suitable monomeric monoisocyanates which can optionally be used in the polyisocyanate composition A) are, for example, n-butyl isocyanate, n-amyl isocyanate, n-hexyl isocyanate, n-heptyl isocyanate, n-octyl isocyanate, undecyl isocyanate, dodecyl isocyanate, tetradecyl isocyanate, cetyl isocyanate, stearyl isocyanate, cyclopentyl isocyanate, cyclohexyl isocyanate, 3- or 4-methylcyclohexyl isocyanate or any desired mixtures of such monoisocyanates. An example of a monomeric isocyanate having an isocyanate functionality greater than two which can optionally be added to the polyisocyanate composition A) is 4-isocyanatomethyloctane 1,8-diisocyanate (triisocyanatononane; TIN).

In one embodiment of the invention, the polyisocyanate composition A) contains not more than 30% by weight, especially not more than 20% by weight, not more than 15% by weight, not more than 10% by weight, not more than 5% by weight or not more than 1% by weight, based in each case on the weight of the polyisocyanate composition A), of aromatic polyisocyanates. As used here, "aromatic polyisocyanate" means a polyisocyanate having at least one aromatically bonded isocyanate group.

Aromatically bonded isocyanate groups are understood to mean isocyanate groups bonded to an aromatic hydrocarbyl radical.

In a preferred embodiment of the process of the invention, a polyisocyanate composition A) having exclusively aliphatically and/or cycloaliphatically bonded isocyanate groups is used.

Aliphatically and cycloaliphatically bonded isocyanate groups are understood to mean isocyanate groups bonded, respectively, to an aliphatic and cycloaliphatic hydrocarbyl radical.

In another preferred embodiment of the process of the invention, a polyisocyanate composition A) consisting of or comprising one or more oligomeric polyisocyanates is used, where the one or more oligomeric polyisocyanates has/have exclusively aliphatically and/or cycloaliphatically bonded isocyanate groups.

In a further embodiment of the invention, the polyisocyanate composition A) consists to an extent of at least 70%, 80%, 85%, 90%, 95%, 98% or 99% by weight, based in each case on the weight of the polyisocyanate composition A), of polyisocyanates having exclusively aliphatically and/or cycloaliphatically bonded isocyanate groups. Practical experiments have shown that particularly good results can be achieved with polyisocyanate compositions A) in which the oligomeric polyisocyanates present therein have exclusively aliphatically and/or cycloaliphatically bonded isocyanate groups.

In a particularly preferred embodiment of the process of the invention, a polyisocyanate composition A) is used which consists of or comprises one or more oligomeric polyisocyanates, where the one or more oligomeric polyisocyanates is/are based on 1,4-diisocyanatobutane (BDI), 1,5-diisocyanatopentane (PDI), 1,6-diisocyanatohexane (HDI), isophorone diisocyanate (IPDI) or 4,4'-diisocyanatodicyclohexylmethane (H12MDI) or mixtures thereof.

In a further embodiment of the invention, the proportion of isocyanurate structures in the polyisocyanurate plastic obtained by the process of the invention is at least 20% by weight, based on the weight of the polyisocyanurate plastic. The proportion of isocyanurate structures in the polyisocyanurate plastic obtained can be determined, for example, via solid-state $^{13}C$ NMR.

In a further embodiment of the invention, polyisocyanate compositions A) with a viscosity greater than 500 mPas and less than 500 000 mPas, preferably greater than 1000 mPas and less than 300 000 mPas, particularly preferably greater than 1000 mPas less than 200 000 mPas, measured to DIN EN ISO 3219 at 21° C., are used in the process of the invention.

The polyisocyanurates of the invention are obtainable by catalytic trimerization by the process of the invention. "Catalytic" here means in the presence of a suitable catalyst B).

Suitable catalysts B) for the process in accordance with the invention are in principle any compounds which accelerate the trimerization of isocyanate groups to isocyanurate structures. Since isocyanurate formation, depending on the catalyst used, is frequently accompanied by side reactions, for example dimerization to give uretdione structures or trimerization to form iminooxadiazinediones (called asymmetric trimers), and, in the presence of urethane groups in the starting polyisocyanate, by allophanatization reactions, the term "trimerization" in the context of the present invention is also to be used synonymously for these oligomerization reactions that proceed additionally.

In a particular embodiment, however, trimerization means that predominantly cyclotrimerizations of at least 50%, preferably at least 60%, more preferably at least 70% and especially at least 80% of isocyanate groups present in the polyisocyanate composition A) to give isocyanurate structural units are catalysed. However, side reactions, especially those to give uretdione, allophanate and/or iminooxadiazinedione structures, typically occur and can even be used in a controlled manner in order to advantageously affect, for example, the $T_g$ value of the polyisocyanurate plastic obtained.

Suitable catalysts B) for the process of the invention are, for example, simple tertiary amines, for example triethylamine, tributylamine, N,N-dimethylaniline, N-ethylpiperidine or N,N'-dimethylpiperazine. Suitable catalysts are also the tertiary hydroxyalkylamines described in GB 2 221 465, for example triethanolamine, N-methyldiethanolamine, dimethylethanolamine, N-isopropyldiethanolamine and 1-(2-hydroxyethyl)pyrrolidine, or the catalyst systems that are known from GB 2 222 161 and consist of mixtures of tertiary bicyclic amines, for example DBU, with simple low molecular weight aliphatic alcohols.

Likewise suitable as trimerization catalysts B) for the process of the invention are a multitude of different metal compounds. Suitable examples are the octoates and naphthenates of manganese, iron, cobalt, nickel, copper, zinc, zirconium, cerium or lead that are described as catalysts in DE-A 3 240 613, or mixtures thereof with acetates of lithium, sodium, potassium, calcium or barium, the sodium and potassium salts of linear or branched alkanecarboxylic acids having up to 10 carbon atoms that are known from DE-A 3 219 608, for example of propionic acid, butyric acid, valeric acid, caproic acid, heptanoic acid, caprylic acid, pelargonic acid, capric acid and undecyl acid, the alkali metal or alkaline earth metal salts of aliphatic, cycloaliphatic or aromatic mono- and polycarboxylic acids having 2 to 20 carbon atoms that are known from EP-A 0 100 129, for example sodium or potassium benzoate, the alkali metal phenoxides known from GB-A 1 391 066 and GB-A 1 386 399, for example sodium or potassium phenoxide, the alkali metal and alkaline earth metal oxides, hydroxides, carbonates, alkoxides and phenoxides known from GB 809 809, alkali metal salts of enolizable compounds and metal salts of weak aliphatic or cycloaliphatic carboxylic acids, for example sodium methoxide, sodium acetate, potassium acetate, sodium acetoacetate, lead 2-ethylhexanoate and lead naphthenate, the basic alkali metal compounds complexed with crown ethers or polyether alcohols that are known from EP-A 0 056 158 and EP-A 0 056 159, for example complexed sodium or potassium carboxylates, the pyrrolidinone-potassium salt known from EP-A 0 033 581, the mono- or polynuclear complex of titanium, zirconium and/or hafnium known from application EP 13196508.9, for example zirconium tetra-n butoxide, zirconium tetra-2-ethylhexanoate and zirconium tetra-2-ethylhexoxide, and tin compounds of the type described in European Polymer Journal, vol. 16, 147-148 (1979), for example dibutyltin dichloride, diphenyltin dichloride, triphenylstannanol, tributyltin acetate, tributyltin oxide, tin octoate, dibutyl(dimethoxy)stannane and tributyltin imidazolate.

Further trimerization catalysts suitable for the process of the invention can be found, for example, in J. H. Saunders and K. C. Frisch, Polyurethanes Chemistry and Technology, p. 94 ff. (1962) and the literature cited therein.

The catalysts B) can be used in the process of the invention either individually or in the form of any desired mixtures with one another.

Preferred catalysts B) are metal compounds of the aforementioned type, especially carboxylates and alkoxides of alkali metals, alkaline earth metals or zirconium, in combination with complexing agents such as crown ethers or polyethylene glycols or polypropylene glycols, and organic tin compounds of the type mentioned.

Particularly preferred trimerization catalysts B) are sodium and potassium salts of aliphatic carboxylic acids having 2 to 20 carbon atoms in combination with complexing agents such as crown ethers or polyethylene glycols or polypropylene glycols, and aliphatically substituted tin compounds.

Very particularly preferred trimerization catalysts B) for the process of the invention are potassium acetate in combination with complexing agents such as crown ethers or polyethylene glycols or polypropylene glycols, tin octoate and/or tributyltin oxide.

In the process of the invention, the trimerization catalyst B) is generally used in a concentration based on the amount of the polyisocyanate composition A) used of 0.0005% to 5.0% by weight, preferably of 0.0010% to 2.0% by weight and more preferably of 0.0015% to 1.0% by weight.

The trimerization catalysts B) used in the process of the invention are generally sufficiently soluble in the polyisocyanate composition A) in the amounts that are required for initiating the trimerization reaction. The catalyst B) is therefore preferably added to the polyisocyanate composition A) in neat form.

Optionally, however, the catalysts B) can also be used dissolved in a suitable organic solvent to improve their incorporability. The dilution level of the catalyst solutions can be freely selected within a very wide range. Catalytically active catalyst solutions are typically those of a concentration over and above about 0.01% by weight.

Suitable catalyst solvents are, for example, solvents that are inert toward isocyanate groups, for example hexane, toluene, xylene, chlorobenzene, ethyl acetate, butyl acetate, diethylene glycol dimethyl ether, dipropylene glycol dimethyl ether, ethylene glycol monomethyl or monoethyl ether acetate, diethylene glycol ethyl and butyl ether acetate, propylene glycol monomethyl ether acetate, 1-methoxyprop-2-yl acetate, 3-methoxy-n-butyl acetate, propylene glycol diacetate, acetone, methyl ethyl ketone, methyl isobutyl ketone, cyclohexanone, lactones such as β-propiolactone, γ-butyrolactone, ε-caprolactone and ε-methylcaprolactone, but also solvents such as N-methylpyrrolidone and N-methylcaprolactam, 1,2-propylene carbonate, methylene chloride, dimethyl sulphoxide, triethyl phosphate or any desired mixtures of such solvents.

If catalyst solvents are used in the process of the invention, preference is given to using catalyst solvents which bear groups reactive toward isocyanates and can be incorporated into the polyisocyanurate plastic. Examples of such solvents are mono or polyhydric simple alcohols, such as e.g. methanol, ethanol, n-propanol, isopropanol, n-butanol, n-hexanol, 2-ethyl-1-hexanol, ethylene glycol, propylene glycol, the isomeric butanediols, 2-ethyl-1,3-hexanediol or glycerol; ether alcohols, such as e.g. 1-methoxy-2-propanol, 3-ethyl-3-hydroxymethyloxetane, tetrahydrofurfuryl alcohol, ethylene glycol monomethyl ether, ethylene glycol monoethyl ether, ethylene glycol monobutyl ether, diethylene glycol monomethyl ether, diethylene glycol monoethyl ether, diethylene glycol monobutyl ether, diethylene glycol, dipropylene glycol or else liquid higher molecular weight polyethylene glycols, polypropylene glycols, mixed polyethylene/polypropylene glycols, and monoalkyl ethers thereof; ester alcohols, such as e.g. ethylene glycol monoacetate, propylene glycol monolaurate, glycerol mono and diacetate, glycerol monobutyrate or 2,2,4-trimethyl-1,3-pentanediol monoisobutyrate; unsaturated alcohols such as e.g. allyl alcohol, 1,1-dimethyl allyl alcohol or oleic alcohol; araliphatic alcohols such as e.g. benzyl alcohol; N-monosubstituted amides, such as e.g. N-methylformamide, N-methylacetamide, cyanoacetamide or 2-pyrrolidinone or any desired mixtures of such solvents.

The polyisocyanurate plastics obtainable by the process of the invention, even as such, i.e. without addition of appropriate auxiliaries and additives C), feature very good light stability. Nevertheless, it is optionally possible to use standard auxiliaries and additives C) as well in the production thereof, for example standard fillers, UV stabilizers, antioxidants, mould release agents, water scavengers, slip additives, defoamers, levelling agents, rheology additives, flame retardants and/or pigments. These auxiliaries and additives C), excluding fillers and flame retardants, are typically present in the polyisocyanurate plastic in an amount of less than 10% by weight, preferably less than 5% by weight, more preferably up to 3% by weight, based on the polyisocyanate composition A). Flame retardants are typically present in the polyisocyanurate plastic in amounts of not more than 70% by weight, preferably not more than 50% by weight and more preferably not more than 30% by weight, calculated as the total amount of flame retardants used, based on the polyisocyanate composition A).

Suitable fillers $C_w$) are, for example AlOH3, CaCO₃, metal pigments such as TiO₂ and further known standard fillers. These fillers $C_w$) are preferably used in amounts of not more than 70% by weight, preferably not more than 50% by weight and more preferably not more than 30% by weight, calculated as the total amount of fillers used, based on the polyisocyanate composition A). Preferred are fillers which do not decrease the transmission values below 70%.

Suitable UV stabilizers $C_x$) may preferably be selected from the group consisting of piperidine derivatives, for example 4-benzoyloxy-2,2,6,6-tetramethylpiperidine, 4-benzoyloxy-1,2,2,6,6-pentamethylpiperidine, bis(2,2,6,6-tetramethyl-4-piperidyl) sebacate, bis(1,2,2,6,6-pentamethyl-1-4-piperidinyl) sebacate, bis(2,2,6,6-tetramethyl-4-piperidyl) suberate, bis(2,2,6,6-tetramethyl-4-piperidyl) dodecanedioate; benzophenone derivatives, for example 2,4-dihydroxy-, 2-hydroxy-4-methoxy-, 2-hydroxy-4-octoxy-, 2-hydroxy-4-dodecyloxy- or 2,2'-dihydroxy-4-dodecyloxybenzophenone; benzotriazole derivatives, for example 2-(2H-benzotriazol-2-yl)-4,6-di-tert-pentylphenol, 2-(2H-benzotriazol-2-yl)-6-dodecyl-4-methylphenol, 2-(2H-benzotriazol-2-yl)-4,6-bis(1-methyl-1-phenylethyl)phenol, 2-(5-chloro-2H-benzotriazol-2-yl)-6-(1,1-dimethylethyl)-4-methylphenol, 2-(2H-benzotriazol-2-yl)-4-(1,1,3,3-tetramethylbutyl)phenol, 2-(2H-benzotriazol-2-yl)-6-(1-methyl-1-phenylethyl)-4-(1,1,3,3-tetramethylbutyl)phenol, isooctyl 3-(3-(2H-benzotriazol-2-yl)-5-(1,1-dimethylethyl)-4-hydroxyphenylpropionate), 2-(2H-benzotriazol-2-yl)-4,6-bis(1,1-dimethylethyl)phenol, 2-(2H-benzotriazol-2-yl)-4,6-bis(1-methyl-1-phenylethyl)phenol, 2-(5-chloro-2H-benzotriazol-2-yl)-4,6-bis(1,1-dimethylethyl)phenol; oxalanilides, for example 2-ethyl-2'-ethoxy- or 4-methyl-4'-methoxyoxalanilide; salicylic esters, for example phenyl salicylate, 4-tert-butylphenyl salicylate, 4-tert-octylphenyl salicylate; cinnamic ester derivatives, for example methyl α-cyano-β-methyl-4-methoxycinnamate, butyl α-cyano-β-methyl-4-methoxycinnamate, ethyl α-cyano-β-phenylcinnamate, isooctyl α-cyano-β-phenylcinnamate; and malonic ester derivatives, such as dimethyl 4-methoxybenzylidenemalonate, diethyl 4-methoxybenzylidenemalonate, dimethyl 4 butoxybenzylidenemalonate. These preferred light stabilizers can be used either individually or in any desired combinations with one another.

Particularly preferred UV stabilizers $C_x$ for the polyisocyanurate plastics producible in accordance with the invention are those which fully absorb light of wavelength <400 nm. These include, for example, the benzotriazole derivatives mentioned. Especially preferred UV stabilizers are 2-(5-chloro-2H-benzotriazol-2-yl)-6-(1,1-dimethylethyl)-4-methylphenol, 2-(2H-benzotriazol-2-yl)-4-(1,1,3,3-tetramethylbutyl)phenol and/or 2-(5-chloro-2H-benzotriazol-2-yl)-4,6-bis(1,1-dimethylethyl)phenol.

It is optionally possible to add one or more of the UV stabilizers $C_x$) mentioned by way of example to the polyisocyanate composition A), preferably in amounts of 0.001% to 3.0% by weight, more preferably 0.01% to 2% by weight, calculated as the total amount of UV stabilizers used, based on the total weight of the polyisocyanate composition A).

Suitable antioxidants $C_y$) are preferably sterically hindered phenols, which may be selected preferably from the group consisting of 2,6-di-tert-butyl-4-methylphenol (ionol), pentaerythritol tetrakis(3-(3,5-di-tert-butyl-4-hydroxyphenyl)propionate), octadecyl 3-(3,5-di-tert-butyl-4-hydroxyphenyl)propionate, triethylene glycol bis(3-tert-butyl-4-hydroxy-5-methylphenyl)propionate, 2,2'-thiobis(4-methyl-6-tert-butylphenol) and 2,2'-thiodiethyl bis[3-(3,5-di-tert-butyl-4-hydroxyphenyl)propionate]. If required, they can be used either individually or in any desired combinations with one another.

These antioxidants $C_y$) are preferably used in amounts of 0.01% to 3.0% by weight, more preferably 0.02% to 2.0% by weight, calculated as the total amount of antioxidants used, based on the polyisocyanate composition A).

The process of the invention can, apart from the small amounts of any catalyst solvents to be used in addition, be conducted in a solvent-free manner. Especially in the case of the inventive use for production of coatings or films, the polyisocyanate component can optionally also be diluted with organic solvents to reduce the processing viscosity. Solvents suitable for this purpose are, for example, the catalyst solvents that are inert toward isocyanate groups and have already been described above.

In the case of the inventive use for production of films, semi-finished products or mouldings, further auxiliaries and additives C) added, finally, may also be internal mould release agents $C_z$).

These are preferably the non-ionic surfactants containing perfluoroalkyl or polysiloxane units known as mould release agents, quaternary alkylammonium salts, such as e.g. trimethylethylammonium chloride, trimethylstearylammonium chloride, dimethylethylcetylammonium chloride, triethyldodecylammonium chloride, trioctylmethylammonium chloride and diethylcyclohexyldodecylammonium chloride, acidic mono and dialkyl phosphates having 2 to 18 carbon atoms in the alkyl radical, such as e.g. ethyl phosphate, diethyl phosphate, isopropyl phosphate, diisopropyl phosphate, butyl phosphate, dibutyl phosphate, octyl phosphate, dioctyl phosphate, isodecyl phosphate, diisodecyl phosphate, dodecyl phosphate, didodecyl phosphate, tridecanol phosphate, bis(tridecanol) phosphate, stearyl phosphate, distearyl phosphate and any desired mixtures of such mould release agents.

Particularly preferred mould release agents $C_z$) are the acidic mono- and dialkyl phosphates mentioned, most preferably those having 8 to 12 carbon atoms in the alkyl radical.

Internal mould release agents $C_z$) are used in the process of the invention, if appropriate, preferably in amounts of 0.01% to 3.0% by weight, more preferably 0.02% to 2.0% by weight, calculated as the total amount of internal mould release agent used, based on the polyisocyanate composition A).

In one embodiment of the process of the invention, a trimerization catalyst B) or a mixture of different trimerization catalysts B) is added to the polyisocyanate composition A) described, optionally under inert gas, for example nitrogen, and optionally with additional use of the aforementioned solvents and auxiliaries and additives C), and mixed in homogeneously with the aid of a suitable mixing unit. The addition of catalyst B) and the solvent to be optionally co used as well as auxiliaries and additives C) can take place here in any desired order one after the other or in a mixture in the aforementioned amounts and usually at a temperature of 0 to 100° C., preferably from 15 to 80° C., particularly preferably from 20 to 60° C. In a particular embodiment of the invention, the reaction mixture thus obtained has a pot life, defined as the time span from the mixing of the polyisocyanate composition A) with the trimerization catalyst B) to the time point at which the viscosity of the reaction mixture is twice the starting value, of greater than 10 min at 23° C. This ensures both certain miscibility and also certain and simple processing without the risk of a reaction proceeding in an uncontrolled manner with the evolution of considerable heat.

The application of the catalysed reaction mixtures thus obtained can be effected by different methods known per se according to the end use. To produce films or coatings, such as e.g. paints, reaction mixtures which comprise the catalyst B) and the polyisocyanate composition A) can be applied for example by spraying, spreading, immersing, flooding or with the help of brushes, rollers or doctor knifes in one or more layers onto any desired substrates, such as e.g. metal, wood, glass, stone, ceramic materials, concrete, rigid and flexible plastics, textiles, leather and paper, which may optionally also be provided with customary primers prior to the coating.

For production of solid bodies, for example semi-finished products or mouldings, reaction mixtures comprising the catalyst B) and the polyisocyanate composition A) may be introduced into open or closed moulds, for example by simple manual pouring, or with the aid of suitable machinery, for example the low-pressure or high-pressure machinery which is standard in polyurethane technology.

Subsequently, the trimerization reaction can be started by heating the coated substrates or filled moulds, the optimum reaction temperature being 20 to 250° C., preferably from 40 to 200° C., particularly preferably from 100 to 190° C., depending on the catalyst selected in each case. Particularly advantageously, the polymerization can be conducted at temperatures above the glass transition point of the desired products. In a particular embodiment of the invention, the temperature of the reaction mixture reaches more than 80° C. in the course of the reaction, but remains below 300° C.

Particularly in the case of thick-layered mouldings, the reaction temperature has an adiabatic component which can lead to temperature peaks in the reaction mixture of +5 to +100° C. compared to the preset reaction temperature (i.e. ambient temperature). The adiabatic component is understood to mean the reaction enthalpy which is not released to the environment by heat transfer but leads to a temperature increase and acceleration of the reaction in the trimerization mixture.

Depending on the catalyst B) chosen and the reaction temperature chosen, the trimerization reaction is very substantially complete, as defined below, after a period of less than one minute up to several hours. In practice, it has been found that the trimerization reaction at reaction temperatures of more than 80° C. is usually largely concluded in less than 12 h. When "reaction temperatures" are being discussed here, this means the ambient temperature. According to a preferred embodiment of the invention, the trimerization reaction at a reaction temperature of greater than 80° C. is concluded in less than 5 h, particularly preferably less than 1 h, very particularly preferably less than 30 min. The progress of the reaction can initially still be determined by titrimetric determination of the NCO content, but gelation and solidification of the reaction mixture sets in rapidly with advancing conversion, which makes wet-chemical analysis methods impossible. The further conversion of isocyanate groups can then only be monitored by spectroscopic methods, for example by IR spectroscopy with reference to the intensity of the isocyanate band at about 2270 $cm^{-1}$.

The polyisocyanurate plastics of the invention are preferably polyisocyanurates with high conversion, i.e. those in which the trimerization reaction to give polyisocyanurate structures is very substantially complete. A trimerization reaction to give polyisocyanurate structures can be regarded as "very substantially complete" in the context of the present invention when at least 80%, preferably at least 90% and more preferably at least 95% of the free isocyanate groups originally present in the polyisocyanate composition A) have reacted. In other words, preferably only not more than 20%, not more than 10% and more preferably not more than 5% of the isocyanate groups originally present in the polyisocyanate composition A) are present in the polyisocyanurate plastic of the invention. This can be achieved by conducting the catalytic trimerization in the process of the invention at least up to a conversion level at which only, for example, not more than 20% of the isocyanate groups originally present in the polyisocyanate composition A) are present, such that a polyisocyanurate with high conversion is obtained. The percentage of isocyanate groups still present can be determined by a comparison of the content of isocyanate groups in % by weight in the original polyisocyanate composition A) with the content of isocyanate groups in % by weight in the reaction product, for example by the aforementioned comparison of the intensity of the isocyanate band at about 2270 $cm^{-1}$ by means of IR spectroscopy.

In a preferred embodiment, the total content of extractable isocyanate-containing compounds in the polyisocyanurate plastic of the invention, based on the polyisocyanate composition A) used, is less than 1% by weight. The total content of extractable isocyanate-containing compounds can take place, in a manner that is particularly relevant in practice, by processes known per se, preferably by extraction with suitable solvents that are inert towards isocyanate groups, for example aliphatic or cycloaliphatic hydrocarbons such as pentane, hexane, heptane, cyclopentane, cyclohexane, toluene or xylene and subsequent determination of the isocyanate group content in the extract, for example by IR spectroscopy.

In a further preferred embodiment, the polyisocyanurate plastics of the invention have a transmittance at a path length of 4 mm of greater than 70%, preferably greater than 80% and more preferably greater than 90%, determined in accordance with ASTM D1003. The process of the invention differs in this respect from the very exothermic prior art processes, in which the significant evolution of heat results in foam formation and discolouration, which greatly reduce transmittance. Besides purely aesthetic applications, a high transmittance is also particularly desirable in order to be better able to identify flaws in mouldings and films.

In another preferred embodiment, the polyisocyanurate plastics of the invention have a b* value determined in accordance with DIN 5033 in the L*a*b colour space of less than 15, preferably less than 10. Every colour in the L*a*b* colour space is defined by a colour locus having the Cartesian coordinates {L*, a*, b*}. The L* axis describes the brightness (luminance) of the colour with values of 0 to 100. The a* axis describes the green or red component of a colour, negative values representing green and positive values representing red. The b* axis describes the blue or yellow component of a colour, negative values representing blue and positive values representing yellow. Relatively high positive b* values therefore indicate significant yellowing which is unwanted for many applications.

With the process of the invention, it is possible in a very efficient manner to obtain homogeneous, blister-free polyisocyanurate plastics. These especially feature a density of greater than 1 $g/cm^3$, determined in accordance with DIN EN ISO 1183-1.

Practical experiments have shown that the polyisocyanurate plastics according to the invention preferably have a hardness, determined according to DIN 53505, of more than 30 Shore D, preferably 50 Shore D, particularly preferably 60 Shore D.

Furthermore, it has been established through practical experiments that the polyisocyanurate plastics according to the invention preferably have a glass transition temperature, determined by means of DSC corresponding to DIN 61006, at a heating rate of 20 K/min, of more than 40° C., preferably more than 50° C., particularly preferably more than 60° C.

The glass transition temperatures ($T_g$) stated here can be determined by means of dynamic differential calorimetry corresponding to DIN EN 61006, method A, using a DSC instrument calibrated with indium and lead and where three directly consecutive passes through a heating run of −50° C. to +200° C., heating rate 20 K/min, with subsequent cooling, cooling rate 320 K/min, are conducted and the first heating curve is used for determining the values and where the temperature at the half height of one glass transition stage is determined as $T_g$.

The polyisocyanurate plastics obtainable by the method of the present invention are preferably characterized by a combination of high transmittance and low b* values. Preferably, they have a transmittance of more than 70% and a b*-value of less than 15. It is particularly advantageous that polyisocyanurate with the aforementioned properties are obtainable within short reaction times. Preferably, the curing of said products takes less than 30 minutes.

The polyisocyanurate plastics obtainable by the process of the invention can advantageously be surface functionalized by methods known to those skilled in the art. This can be performed for example by means of coating processes or reactive functionalization, in each case with or without primer.

The process of the invention produces transparent, yellowing-stable polyisocyanurate plastics with low-level discoloration which, depending on the type of polyisocyanate composition A) used, optionally contain further oligomeric structures besides isocyanurate structures and are characterized by exceptional heat stabilities.

The process of the invention makes it possible, in a simple manner, to synthesize highly converted polyisocyanurate plastics through suitable selection of starting polyisocyanates at high temperatures and with short reaction times.

In contrast to polyisocyanurate plastics which have been produced starting from monomeric aliphatic diisocyanates, such as e.g. HDI, the process products according to the invention are characterized, for example, by a deviating glass transition temperature ($T_g$). The comparatively little heat of reaction released also allows the problem-free production of solid blister-free large-volume mouldings.

The invention is elucidated in detail hereinafter with reference to examples.

EXAMPLES

Example 1: Comparison of Isocyanurate Polymers Made from Different Polyisocyanates All percentages are based on weight, unless stated otherwise.

The pot life was measured after removal of a 1 ml sample from the freshly mixed reaction mixture in a Physica MCR 51 rheometer at RT. The pot life has been attained when the starting viscosity has doubled.

The NCO contents were determined by titrimetric means to DIN EN ISO 11909.

All the viscosity measurements were made with a Physica MCR 51 rheometer from Anton Paar Germany GmbH (DE) to DIN EN ISO 3219.

The densities of the starting polyisocyanates were determined to DIN EN ISO 2811, and those of the cured polyisocyanurate plastics to DIN EN ISO 1183-1.

The glass transition temperature $T_g$ was determined by means of DSC (differential scanning calorimetry) with a Mettler DSC 12E (Mettler Toledo GmbH, Giessen, Germany) in accordance with DIN EN 61006. Calibration was effected via the melt onset temperature of indium and lead. 10 mg of substance were weighed out in standard capsules. The measurement was effected by three heating runs from −50° C. to +200° C. at a heating rate of 20 K/min with subsequent cooling at a cooling rate of 320 K/min. Cooling was effected by means of liquid nitrogen. The purge gas used was nitrogen. The values stated in the table below are based in each case on the evaluation of the 1st heating curve since in the investigated reactive systems, changes in the sample are possible in the measuring process at high temperatures as a result of the thermal stress in the DSC. The glass transition temperature $T_g$ determined was the temperature at half the height of a glass transition step.

Shore hardnesses were measured to DIN 53505 with the aid of a Zwick 3100 Shore hardness tester (from Zwick, Germany) at 23° C. and 50% air humidity.

The contents (mol %) of the uretdione, isocyanurate, allophanate, biuret, iminooxadiazinedione and/or oxadiazinetrione structures present in the starting polyisocyanates were calculated from the integrals of proton-decoupled $^{13}C$ NMR spectra (recorded on a Bruker DPX-400 instrument) and are each based on the sum total of uretdione, isocyanurate, allophanate, biuret, iminooxadiazinedione and/or oxadiazinetrione structures present. In the case of HDI polyisocyanates, the individual structural elements have the following chemical shifts (in ppm): Uretdione: 157.1; Isocyanurate: 148.4; Allophanate: 155.7 and 153.8, Biuret: 155.5; Iminooxadiazinedione: 147.8, 144.3 and 135.3; Oxadiazinetrione: 147.8 and 143.9.

IR spectra were recorded on a Spectrum Two FT-IR spectrometer equipped with an ATR unit from Perkin Elmer, Inc.

Transmittance was measured with a Byk-Gardner hazegard plus instrument according to ASTM D1003 on specimens of thickness 4 mm.

Discolourations were measured in accordance with DIN 5033 Part 7 on a CM-5 spectrophotometer using specimens of thickness 4 mm without gloss at a viewing angle of 8° and with diffuse illumination.

Extractable isocyanates were ascertained following coarse comminution of the specimen into parts with a volume less than 0.5 cm$^3$. 10 g were taken from this in the form of the comminuted fragments and extracted with 50 ml of PA quality toluene with stirring at 23° C. over the course of 24 h. The extract was filtered and examined for extractable components against the toluene used for the extraction by means of GC/MS/EI testing. The concentration figures result from a GC flame ionization detection (FID); the compounds found in the GC were identified by means of MS spectroscopy. Injection volume was 0.2 microlitres, the procedure was in accordance with Method 2301-0291701-04D from the supplier Currenta GmbH & Co. OHG.

Inventive Process 100 g of the starting polyisocyanate are weighed into a polypropylene cup together with a catalyst mixture consisting of 0.177 g of potassium acetate, 0.475 g of [18]crown-6 and 3.115 g of diethylene glycol (sourced from Sigma-Aldrich in PA qualities and used as supplied), and homogenized at 2750 rpm with the aid of a Speed-Mixer DAC 150 FVZ (from Hauschild, Germany) for 1 min. 16 g of the contents of each polypropylene cup are weighed into an aluminium dish of diameter 6.3 cm and depth 1 cm which, for better demoulding, had previously been rubbed with 1% soya lecithin W250 in ethyl acetate solution and dried. The aluminium dish thus filled is heated in a drying cabinet at 180° C. for 15 min. After cooling to room temperature, the specimen is demoulded. Specimens of thickness about 0.4 cm are obtained, which slightly increase in thickness toward the beaker edge.

The process of the invention is employed for production both of inventive and noninventive polyisocyanurate plastics.

All of the polyisocyanates used were acquired from Bayer MaterialScience AG, Leverkusen, Germany and are either commercially available or can be produced by processes described in the patent literature on the basis of readily available monomers and catalysts.

Starting Compounds:

Inventive Starting Polyisocyanate A

HDI polyisocyanate containing isocyanurate groups, prepared in accordance with Example 11 of EP-A 330 966, with the alteration that the catalyst solvent used was 2-ethylhexanol rather than 2-ethylhexane-1,3-diol. The reaction was stopped at an NCO content of the crude mixture of 42% by adding dibutyl phosphate. Subsequently, unconverted HDI was removed by thin-film distillation at a temperature of 130° C. and a pressure of 0.2 mbar.
NCO content: 23.0%
NCO functionality: 3.2
Monomeric HDI: 0.1%
Viscosity (23° C.): 1200 mPas
Density (20° C.): 1.17 g/cm$^3$
Distribution of the oligomeric structure types:
Isocyanurate: 89.7 mol %
Iminooxadiazinedione 2.5 mol %
Uretdione 2.7 mol %
Allophanate: 5.1 mol %

Inventive Starting Polyisocyanate B

HDI polyisocyanate containing isocyanurate groups, prepared in accordance with Example 11 of EP-A 330 966. The reaction was stopped at an NCO content of the crude mixture of 40% by adding dibutyl phosphate. Subsequently, unconverted HDI was removed by thin-film distillation at a temperature of 130° C. and a pressure of 0.2 mbar.
NCO content: 21.8%
NCO functionality: 3.4
Monomeric HDI: 0.1%
Viscosity (23° C.): 3000 mPas
Density (20° C.): 1.17 g/cm$^3$
Distribution of the oligomeric structure types:
Isocyanurate: 84.5 mol %
Iminooxadiazinedione 5.4 mol %
Uretdione 2.9 mol %
Allophanate: 7.2 mol %

Inventive Starting Polyisocyanate C

Isophorone diisocyanate (IPDI), in accordance with Example 2 of EP-A 0 003 765, was trimerized down to an NCO content of 31.1% and the excess IPDI was removed by thin-film distillation at 170° C./0.1 mbar. This gave an isocyanurate polyisocyanate as a virtually colourless solid resin having a melting range of 100 to 110° C.
NCO content: 16.4%
NCO functionality: 3.3
Monomeric IPDI: 0.2%

70 parts by weight of the solid IPDI polyisocyanurate were coarsely comminuted and introduced into a reaction vessel at room temperature together with 30 parts by weight of the starting polyisocyanate A1) under N2 atmosphere. To dissolve the solid resin and homogenize the mixture, it was heated to 100-140° C. and stirred until a virtually clear solution was obtained. Then, the mixture was cooled to 50° C. and filtered over a 200μ filter.
NCO content: 21.2%
NCO functionality: 3.2
Monomeric IPDI: 0.1%
Monomeric HDI: 0.1
Distribution of the oligomeric structure types:
Isocyanurate: 92.1 mol %
Iminooxadiazinedione 1.8 mol %
Uretdione 1.9 mol %
Allophanate: 4.2 mol %

Inventive Starting Polyisocyanate D

The starting polyisocyanate D used was a mixture of 95% by weight of starting isocyanate B and 5% by weight of hexamethylene diisocyanate (HDI).

Inventive Starting Polyisocyanate E

The starting isocyanate E used was a mixture of 90% by weight of starting isocyanate B and 10% by weight of butanediol.

Noninventive Starting Polyisocyanate F

HDI polyisocyanate containing biuret groups, produced in accordance with the process of EP-A 0 150 769 by reaction of 8.2 mol of HDI with 1.0 mol of water in the presence of 0.05 mol of pivalic anhydride at a temperature of 125° C. After reaching a NCO content of 36.6%, unreacted HDI was removed together with pivalic anhydride by thin-film distillation at a temperature of 130° C. and a pressure of 0.2 mbar.
NCO content: 23.0%
NCO functionality: 3.2
Monomeric HDI: 0.4%
Viscosity (23° C.): 2500 mPas
Density (20° C.): 1.13 g/cm$^3$
Distribution of the oligomeric structure types:
Biuret: 87.7 mol %
Uretdione 12.3 mol %

Noninventive Starting Polyisocyanate G

HDI polyisocyanate containing isocyanurate and uretdione groups, prepared by tributylphosphine-catalysed oligomerization in accordance with Example 1a) of EP-A 0 377 177, with the alteration that no 2,2,4-trimethylpentane-1,3-diol was used. The reaction was stopped at an NCO content of 42%, and unconverted HDI was removed by thin-film distillation at a temperature of 130° C. and a pressure of 0.2 mbar.
NCO content: 22.7%
NCO functionality: 2.2
Monomeric HDI: 0.3%
Viscosity (23° C.): 90 mPas
Density (20° C.): 1.13 g/cm$^3$
Distribution of the oligomeric structure types:
Isocyanurate: 15.6 mol %
Iminooxadiazinedione 6.3 mol %
Uretdione 78.1 mol %

Noninventive Starting Polyisocyanate H

HDI polyisocyanate containing isocyanurate and iminooxadiazinedione groups, prepared in accordance with Example 4 of EP-A 0 962 455, by trimerization of HDI using a 50% solution of tetrabutylphosphonium hydrogendifluoride in isopropanol/methanol (2:1) as catalyst. The reaction was stopped at an NCO content of the crude mixture of 43% by adding dibutyl phosphate. Subsequently, unconverted HDI was removed by thin-film distillation at a temperature of 130° C. and a pressure of 0.2 mbar.
NCO content: 23.4%
NCO functionality: 3.2
Monomeric HDI: 0.2%
Viscosity (23° C.): 700 mPas
Density (20° C.): 1.15 g/cm$^3$ Distribution of the oligomeric structure types:
Isocyanurate: 49.9 mol %
Iminooxadiazinedione 45.3 mol %
Uretdione 4.8 mol %

Noninventive Starting Polyisocyanate I

The starting polyisocyanate I used was hexamethylene diisocyanate (available from Bayer Material Science AG, Leverkusen, Germany) as Desmodur H.

Noninventive Starting Polyisocyanate J

The starting polyisocyanate J used was a polyisocyanate containing exclusively urethane structure (available as Desmodur XP 2617 from Bayer Material Science AG, Leverkusen, Germany).
NCO content: 12.5%
NCO functionality: 2.1
Monomeric HDI: <0.5%
Viscosity (23° C.): 4250 mPas
Density (20° C.): 1.09 g/cm$^3$
Distribution of the oligomeric structure types:
Isocyanurate: 0 mol %
Urethane: 100 mol %

Inventive Starting Polyisocyanate K

The starting isocyanate A used was distilled to yield a fraction with >99% Polyisocyanurate Trimer of HDI according to $^{13}$C NMR spectroscopy. NCO content: 24.8%
NCO functionality: 3.0
Monomeric HDI: <0.1%
Viscosity (23° C.): 700 mPas
Density (20° C.): 1.17 g/cm$^3$
Distribution of the oligomeric structure types:
Isocyanurate: 99.2 mol %
Iminooxadiazinedione+Uretdione+Allophanate <1 mol %

The table which follows shows characteristic properties of the polyisocyanurate plastics obtained or products of the process of the invention based on inventive (A-E, and K) and noninventive (F-J)* starting polyisocyanates.

polyisocyanurate plastics exhibit good mechanical properties and thermal stability, which are indicated by a hardness of greater than 50 Shore D and a $T_g$ well above 40° C., i.e. well above room temperature. Inventive polyisocyanurate plastics from the process of the invention, by comparison with the noninventive products made from the starting polyisocyanates F*-J*, additionally feature b* values of less than 15 in the L*a*b colour space and hence a desirable negligibly low discoloration.

The noninventive products, which either remain liquid, decompose during the reaction and have a clearly visible yellowing or cure in an uncontrolled manner and incompletely to give foams with a density of less than 1 g/cm$^3$ are completely unsuitable for the desired use for producing coatings, films, semi-finished products or moldings.

The invention claimed is:

1. A process for producing polyisocyanurate plastics, comprising the following steps:
   a) providing a polyisocyanate composition A) which contains oligomeric polyisocyanates and is low in monomeric diisocyanates, having an isocyanurate structure content in the polyisocyanate composition A) of at least 50 mol %, based on the sum total of oligomeric structures from the group consisting of uretdione, isocyanurate, allophanate, biuret, iminooxadiazinedione and oxadiazinetrione structure that are present in the polyisocyanate composition A);
   b) catalytically trimerizing the polyisocyanate composition A), where
      (i) the catalytic trimerization is conducted at ambient temperatures of at least 80° C.;
      (ii) the catalytic trimerization is conducted within less than 12 hours at least up to a degree of conversion at which only still not more than 20% of the isocyanate groups originally present in the polyisocyanate composition A) are present.

| Starting polyiso-cyanate | Pot-life/ min | Density [g/cm$^3$] | $T_g$ [° C.] | Trans-mittance [%] | L | a | b | Hardness Shore D | Residual isocyanate by IR [%] | Extractable isocyanates (GC/MS) [%] | Observation/explanation |
|---|---|---|---|---|---|---|---|---|---|---|---|
| A | >10 | 1.23 | 109 | 83 | 94 | 0.2 | 6.5 | 72 | <5% | 0% | Extractable fractions <0.3% |
| B | >10 | 1.23 | 106 | 83 | 96 | 0.1 | 5.9 | 73 | <5% | 0% | found and identified in the |
| C | >10 | 1.18 | 171 | 85 | 94 | −0.4 | 5.8 | 87 | <10% | 0% | GC/MS spectrum come from the |
| D | >10 | 1.17 | 108 | 81 | 93 | 0.1 | 7.1 | 84 | <5% | 0% | trimerization catalyst used. |
| E | >10 | 1.28 | 53 | 85 | 98 | −0.1 | 4.0 | 82 | <5% | 0% | |
| F* | >10 | — | — | — | — | — | — | — | >20% | 100% | Remains liquid, significant yellowing |
| G* | >10 | — | — | — | — | — | — | — | >20% | 100% | Remains liquid, significant yellowing |
| H* | >10 | — | — | — | — | — | — | — | >20% | >50% | Remains gel-like/viscous - slight yellowing |
| I* | <10 | <0.5 | — | — | — | — | — | — | — | >5% | Reaction starts immediately after mixing at RT, producing a brown/black foam |
| J* | >10 | 1.08 | 19 | 88 | 95 | −7.2 | 25.3 | 38 | <5% | 0% | Very soft material with significant yellowing |
| K | >10 | 1.23 | 114 | 86 | 95 | −0.1 | 2.9 | 80 | <5% | 0% | Clear and colorless |

*comparative experiments

The results in the table show that the polyisocyanurate plastics of the invention based on the inventive starting polyisocyanates A-E and K which have been produced by the process of the invention, by contrast with the noninventive products produced on the basis of the noninventive starting polyisocyanates F*-I*, feature a low level of extractable isocyanate-containing components. For the processing of the inventive starting polyisocyanates, important pot lives of more than 10 min were obtained, and the resulting 2. The process according to claim 1, wherein the catalytic trimerization is conducted within less than 5 hours, at least up to the degree of conversion specified in step b) (ii).

3. The process according to claim 1, wherein the degree of conversion specified in step b) (ii) is a degree of conversion at which only still not more than 10% of the isocyanate groups originally present in the polyisocyanate composition A) are present.

4. The process according to claim 1, wherein the degree of conversion specified in step b) (ii) is a degree of conversion at which only still not more than 5% of the isocyanate groups originally present in the polyisocyanate composition A) are present.

5. The process according to claim 1, wherein the polyisocyanate composition A) consists of at least 80 by weight, based on the weight of the polyisocyanate composition A), of polyisocyanates which have exclusively aliphatically or cycloaliphatically bonded isocyanate groups.

6. The process according to claim 1, wherein the polyisocyanate composition A) consists of at least 95% by weight, based on the weight of the polyisocyanate composition A), of polyisocyanates which have exclusively aliphatically or cycloaliphatically bonded isocyanate groups.

7. The process according to claim 1, wherein the polyisocyanate composition A) consists of 100% by weight, based on the weight of the polyisocyanate composition A), of polyisocyanates which have exclusively aliphatically or cycloaliphatically bonded isocyanate groups.

8. The process according to claim 1, wherein the oligomeric polyisocyanates consist of one or more oligomeric polyisocyanates which are composed of 1,4-diisocyanatobutane, 1,5-diisocyanatopentane, 1,6-diisocyanatohexane, isophorone diisocyanate or 4,4'-diisocyanatodicyclohexylmethane or mixtures thereof.

9. The process according to claim 1, wherein the polyisocyanate composition A) has a mean NCO functionality of 2.0 to 5.0.

10. The process according to claim 1, wherein the polyisocyanate composition A) has a content of isocyanate groups of 8.0 to 28.0% by weight, based on the weight of the polyisocyanate composition A).

11. The process according to claim 1, wherein said low in monomeric diisocyanates means that the polyisocyanate composition A) has a content of monomeric diisocyanates of not more than 20% by weight, based on the weight of the polyisocyanate composition A).

12. The process according to claim 1, wherein said low in monomeric diisocyanates means that the polyisocyanate composition A) has a content of monomeric diisocyanates of not more than 5% by weight, based on the weight of the polyisocyanate composition A).

13. The process according to claim 1, wherein the proportion of isocyanurate structures in the polyisocyanurate plastic obtained is at least 20% by weight, based on the weight of the polyisocyanurate plastic.

14. A solid body made from an polyisocyanurate plastic obtained by a process comprising the following steps:
  a) providing a polyisocyanate composition A) which contains oligomeric polyisocyanates and is low in monomeric diisocyanates, having an isocyanurate structure content in the polyisocyanate composition A) of at least 50 mol %, based on the sum total of-oligomeric structures from the group consisting of uretdione, isocyanurate, allophanate, biuret, iminooxadiazinedione and oxadiazinetrione structure that are present in the polyisocyanate composition A);
  b) catalytically trimerizing the polyisocyanate composition A), where
    (i) the catalytic trimerization is conducted at ambient temperatures of at least 80° C.;
    (ii) the catalytic trimerization is conducted within less than 12 hours at least up to a degree of conversion at which only still not more than 5% of the isocyanate groups originally present in the polyisocyanate composition A).

15. The solid body according to claim 14, where the proportion of extractable, isocyanate-containing constituents is less than 1% by weight, based on the weight of the originally used polyisocyanate composition A).

16. The solid body according to claim 14, wherein the polyisocyanurate plastic has a transmittance at a path length of 4 mm of greater than 70% determined in accordance with ASTM D1003.

17. The solid body according to claim 14, wherein the polyisocyanurate plastic has a b* value determined according to DIN 5033 in the L*a*b* colour space of less than 15.

18. The solid body according to claim 14, wherein the polyisocyanurate plastic has a density of greater than 1 g/cm$^3$ determined according to DIN EN ISO 1183-1.

19. The solid body according to claim 14, wherein the solids body is a selected from the group consisting of coatings.

20. The solid body according to claim 14, wherein the polyisocyanurate plastic has a transmittance at a path length of 4 mm of greater than 70% determined in accordance with ASTM D1003, wherein the polyisocyanurate plastic has a b* value determined according to DIN 5033 in the L*a*b* colour space of less than 15, and wherein the polyisocyanurate plastic has a density of greater than 1 g/cm$^3$ determined according to DIN EN ISO 1183-1.

* * * * *